(12) United States Patent
Floeter

(10) Patent No.: US 10,930,437 B2
(45) Date of Patent: Feb. 23, 2021

(54) CAPACITOR STACK INSULATION

(71) Applicant: Cardiac Pacemakers, Inc., St. Paul, MN (US)

(72) Inventor: Aaron Louis Floeter, Waconia, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 269 days.

(21) Appl. No.: 15/949,441

(22) Filed: Apr. 10, 2018

(65) Prior Publication Data

US 2018/0294103 A1 Oct. 11, 2018

Related U.S. Application Data

(60) Provisional application No. 62/484,187, filed on Apr. 11, 2017.

(51) Int. Cl.
| | |
|---|---|
| *H01G 4/30* | (2006.01) |
| *H01G 4/224* | (2006.01) |
| *H01G 4/005* | (2006.01) |
| *A61N 1/39* | (2006.01) |
| *H01G 4/18* | (2006.01) |
| *H01G 4/228* | (2006.01) |
| *H01G 4/38* | (2006.01) |
| *H01G 4/232* | (2006.01) |
| *H01G 2/10* | (2006.01) |

(52) U.S. Cl.
CPC ............. *H01G 4/30* (2013.01); *A61N 1/3968* (2013.01); *H01G 2/106* (2013.01); *H01G 4/005* (2013.01); *H01G 4/18* (2013.01); *H01G 4/224* (2013.01); *H01G 4/228* (2013.01); *H01G 4/232* (2013.01); *H01G 4/38* (2013.01); *A61N 1/3956* (2013.01)

(58) Field of Classification Search
CPC .......... H01G 4/30; H01G 2/106; H01G 4/005; H01G 4/18; H01G 4/224; H01G 4/228; H01G 4/232; H01G 4/38; A61N 1/3956; A61N 1/3968

See application file for complete search history.

(56) References Cited

U.S. PATENT DOCUMENTS

| | | | |
|---|---|---|---|
| 5,371,650 A | * | 12/1994 | Lavene .................. H01G 4/224 29/25.42 |
| 7,699,899 B2 | | 4/2010 | Dombro et al. |
| 7,733,631 B2 | | 6/2010 | Brabeck et al. |

(Continued)

OTHER PUBLICATIONS

Vedoy, Arild, "Battery Lithium Cluster Growth Control, U.S. Appl. No. 62/330,317, filed May 2, 2016".

*Primary Examiner* — Lindsey G Wehrheim
(74) *Attorney, Agent, or Firm* — Schwegman Lundberg & Woessner, P.A.

(57) ABSTRACT

A medical device capacitor assembly can include a capacitor including a plurality of anodes and cathodes, wherein the capacitor has a first major face, a second major face opposite the first major face, and a third face extending between the first major face and the second major face. A first insulating film can be sized and shaped to assemble against the first major face, and can include a first set of flaps sized and shaped to cover at least a portion of the third face. A second insulating film sized and shaped to assemble against the second major face, and can include a second set of flaps sized and shaped to cover at least a portion of the third face.

17 Claims, 9 Drawing Sheets

(56) References Cited

U.S. PATENT DOCUMENTS

| | | |
|---|---|---|
| 8,040,659 B2 | 10/2011 | Brabeck et al. |
| 8,974,949 B2 | 3/2015 | Kuhn et al. |
| 2009/0000090 A1* | 1/2009 | Dombro .............. H01G 2/106 29/25.03 |
| 2010/0232089 A1 | 9/2010 | Brabeck et al. |
| 2012/0270091 A1 | 10/2012 | Kuhn et al. |

* cited by examiner

CAPACITOR STACK INSULATION

CLAIM OF PRIORITY

This application claims the benefit of priority under 35 U.S.C. § 119(e) of U.S. Provisional Patent Application Ser. No. 62/484,187, filed on Apr. 11, 2017, which is herein incorporated by reference in its entirety.

TECHNICAL FIELD

This document relates generally to medical devices, and more particularly, but not by way of limitation, to systems, devices, and methods to insulate stacked capacitors.

BACKGROUND

Medical devices such as implantable defibrillators can include a capacitor that is configured to deliver a therapeutic energy pulse (e.g., a defibrillation shock) to a patient to treat a detected arrhythmia. A capacitor can be fabricated by stacking a plurality of anodes and cathodes on top of each other. The capacitor can be insulated to prevent electrical communication between the capacitor and other device components.

SUMMARY

This document discusses, among other things, systems and methods to insulate a capacitor.

An example (e.g., "Example 1") of subject matter (e.g., an apparatus) may include a capacitor assembly. The capacitor assembly can include a capacitor, a first insulating film, or a second insulating film. The capacitor can include a plurality of anodes and cathodes. The capacitor can have a first major face, a second major face opposite the first major face, and a third face extending between the first major face and the second major face. The first insulating film can be sized and shaped to assemble against the first major face. The first insulating film can include a first set of flaps sized and shaped to cover at least a portion of the third face. The second insulating film can be sized and shaped to assemble against the second major face. The second insulating film can include a second set of flaps sized and shaped to cover at least a portion of the third face.

In Example 2, the subject matter of Example 1 may optionally be configured such that the second set of flaps overlaps the first set of flaps.

In Example 3, the subject matter of any one or more of Examples 1-2 may optionally be configured such that the first insulating film is bonded to the stacked capacitor with an adhesive.

In Example 4, the subject matter of any one or more of Examples 1-3 may optionally be configured such that the second insulating film is bonded to the capacitor and to overlapped portions of the first insulating film with an adhesive.

In Example 5, the subject matter of any one or more of Examples 1-4 may optionally be configured such that one or more of the second set of flaps extend over the third face and onto a portion of the third face that is not covered by the first insulating film.

In Example 6, the subject matter of any one or more of Examples 1-5 may optionally be configured such that each of the flaps has a flap width, and the flap width varies as a function of a radius of curvature of an edge of the stacked capacitor.

In Example 7, the subject matter of any one or more of Examples 1-6 may optionally be configured such that the capacitor has a belly portion having a first radius and a corner portion having a second radius that is less than the first radius, and further comprising belly flaps sized and shaped to cover the belly portion and corner flaps sized and shaped to cover the corner portion.

An example (e.g., "Example 8") of subject matter (e.g., a system) may include an implantable medical device. The implantable medical device can include an implantable medical device housing, a pulse generator circuit, a capacitor housing, a stacked capacitor, or one or more insulating films. The pulse generator circuit can be located in the implantable medical device housing. The capacitor housing can be located in the implantable medical device housing. The stacked capacitor can be located in the capacitor housing. The stacked capacitor can be operatively coupled to the pulse generator circuit. The one or more insulating films can extend over top and bottom portions of the stacked capacitor. The one or more insulating films can include a first set of flaps extending down from the top portion over an edge portion of the stacked capacitor. The one or more insulating films can include a second set of flaps extending up from the bottom portion over the edge portion. The first set of flaps and second set of flaps can overlap on the edge portion.

In Example 9, the subject matter of Example 8 may optionally be configured such that the one or more insulating films are configured to prevent electrical communication between the capacitor housing and the stacked capacitor.

In Example 10, the subject matter of any one or more of Examples 8-9 may optionally be configured such that the first set of flaps define gaps between the flaps and the second set of flaps extend over the gaps.

In Example 11, the subject matter of any one or more of Examples 8-10 may optionally be configured such that the stacked capacitor includes a plurality of stacked cathodes and anodes, the edge portion of the stacked capacitor defined by edges of the stacked cathodes, and wherein the first set of flaps and second set up flaps together cover the edges of the stacked cathodes to insulate the edge portion.

In Example 12, the subject matter of any one or more of Examples 8-11 may optionally be configured such that each of the flaps of the first and second set of flaps has a flap width, and the flap width varies as a function of a radius of curvature of an edge of the stacked capacitor.

An example (e.g., "Example 13") of subject matter (e.g., a method) may include a method for insulating a stacked capacitor. The method for insulating a stacked capacitor can include coupling an inner portion of a first insulating film to a first major surface of the stacked capacitor. The method for insulating a stacked capacitor can include folding a first set of flaps of the first insulating film onto a perimeter portion of the stacked capacitor. The method for insulating a stacked capacitor can include coupling an inner portion of a second insulating film to a second major surface of the stacked capacitor. The method for insulating a stacked capacitor can include folding a second set of flaps of the second insulating film onto the perimeter portion of the stacked capacitor.

In Example 14, the subject matter of Examples 13 may optionally be configured such that folding the second set of flaps over gaps between the first set of flaps to fully cover the perimeter portion of the stacked capacitor.

In Example 15, the subject matter of any one or more of Examples 13-14 may optionally be configured such that coupling the inner portion of the first insulating film to the first major surface of the capacitor includes bonding the inner portion of the first insulating film to the first major surface of the stacked capacitor with an adhesive.

An example (e.g., "Example 16") of subject matter (e.g., an apparatus) may include a medical device capacitor assembly. The medical device capacitor assembly can include a capacitor, a first insulating film, or a second insulating film. The capacitor can include a plurality of anodes and cathodes. The capacitor can have a first major face, a second major face opposite the first major face, and a third face extending between the first major face and the second major face. The first insulating film can be sized and shaped to cover the first major face. The first insulating film can include a first set of flaps sized and shaped to cover at least a portion of the third face. The second insulating film can be sized and shaped to cover the second major face. The second insulating film can include a second set of flaps sized and shaped to cover at least a portion of the third face.

In Example 17, the subject matter of Example 16 may optionally be configured such that the second set of flaps overlaps the first set of flaps.

In Example 18, the subject matter of any one or more of Examples 16-17 may optionally be configured such that the first insulating film is bonded to the capacitor with an adhesive.

In Example 19, the subject matter of any one or more of Examples 16-18 may optionally be configured such that the second insulating film is bonded to the capacitor and to overlapped portions of the first insulating film with an adhesive.

In Example 20, the subject matter of any one or more of Examples 16-19 may optionally be configured such that one or more of the second set of flaps extend over the third face and onto a portion of the third face that is covered by the first insulating film.

In Example 21, the subject matter of any one or more of Examples 16-20 may optionally be configured such that the third face is curved.

In Example 22, the subject matter of any one or more of Examples 16-20 may optionally be configured such that the capacitor further includes a fourth face that is not curved, and the first insulating film includes one or more flaps extending over the fourth face.

In Example 23, the subject matter of any one or more of Examples 16-20 may optionally be configured such that each of the flaps has a flap width, and the flap width varies as a function of a radius of curvature of an edge of the capacitor.

In Example 24, the subject matter of any one or more of Examples 16-20 may optionally be configured such that the first insulating film or the second insulating film include one or more alignment features configured to orientate the first insulating film or the second insulating film with respect to the capacitor.

In Example 25, the subject matter of any one or more of Examples 16-20 may optionally be configured such that the capacitor has a belly portion having a first radius and a corner portion having a second radius that is less than the first radius, and further comprising belly flaps sized and shaped to cover the belly portion and corner flaps sized and shaped to cover the corner portion.

In Example 26, the subject matter of any one or more of Examples 16-20 may optionally be configured such that the first insulating film or the second insulating film includes a polymer.

An example (e.g., "Example 27") of subject matter (e.g., a system) may include an implantable medical device. The implantable medical device can include an implantable medical device housing, a pulse generator, a capacitor housing, a capacitor, or one or more insulating films. The pulse generator circuit can be located in the implantable medical device housing. The capacitor housing can be located in the implantable medical device housing. The capacitor can be located in the capacitor housing. The capacitor can be operatively coupled to the pulse generator circuit. The one or more insulating films can extend over top and bottom portions of the capacitor. The one or more films can include a first set of flaps extending down from the top portion over an edge portion of the capacitor. The one or more insulating films can include a second set of flaps extending up from the bottom portion over the edge portion. The first set of flaps and second set of flaps can overlap on the edge portion.

In Example 28, the subject matter of Example 27 may optionally be configured such that the one or more insulating films are configured to prevent electrical communication between the capacitor housing and the capacitor.

In Example 29, the subject matter of any one or more of Examples 27-28 may optionally be configured such that the first set of flaps define gaps between the flaps and the second set of flaps extend over the gaps.

In Example 30, the subject matter of any one or more of Examples 27-29 may optionally be configured such that the capacitor includes a plurality of stacked cathodes and anodes, the edge portion of the capacitor defined by edges of the stacked cathodes, and wherein the first set of flaps and second set up flaps together cover the edges of the stacked cathodes to insulate the edge portion.

In Example 31, the subject matter of any one or more of Examples 27-30 may optionally be configured such that each of the flaps of the first and second set of flaps has a flap width, and the flap width varies as a function of a radius of curvature of an edge of the capacitor.

In Example 32, the subject matter of any one or more of Examples 27-31 may optionally be configured such that the capacitor has a belly portion having a first radius and a corner portion having a second radius that is less than the first radius, and further comprising belly flaps sized and shaped to cover the belly portion and corner flaps sized and shaped to cover the corner portion.

An example (e.g., "Example 33") of subject matter (e.g., a method) may include method for insulating a stacked capacitor. The method for insulating a stacked capacitor can include coupling an inner portion of a first insulating film to a first major surface of the stacked capacitor. The method for insulating a stacked capacitor can include folding a first set of flaps of the first insulating film onto a perimeter portion of the stacked capacitor. The method for insulating a stacked capacitor can include coupling an inner portion of a second insulating film to a second major surface of the stacked capacitor. The method for insulating a stacked capacitor can include folding a second set of flaps of the second insulating film onto the perimeter portion of the stacked capacitor.

In Example 34, the subject matter of Example 33 may optionally be configured such that folding the second set of flaps over gaps between the first set of flaps to fully cover the perimeter portion of the stacked capacitor.

In Example 35, the subject matter of any one or more of Examples 33-34 may optionally be configured such that coupling the inner portion of the first insulating film to the first major surface of the capacitor includes bonding the inner portion of the first insulating film to the first major surface of the stacked capacitor with an adhesive.

An example (e.g., "Example 36") of subject matter (e.g., a system or apparatus) may optionally combine any portion or combination of any portion of any one or more of Examples 1-35 to include "means for" performing any portion of any one or more of the functions or methods of Examples 1-35, or a "machine-readable medium" (e.g., massed, non-transitory, etc.) including instructions that, when performed by a machine, cause the machine to perform any portion of any one or more of the functions or methods of Examples 1-35.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
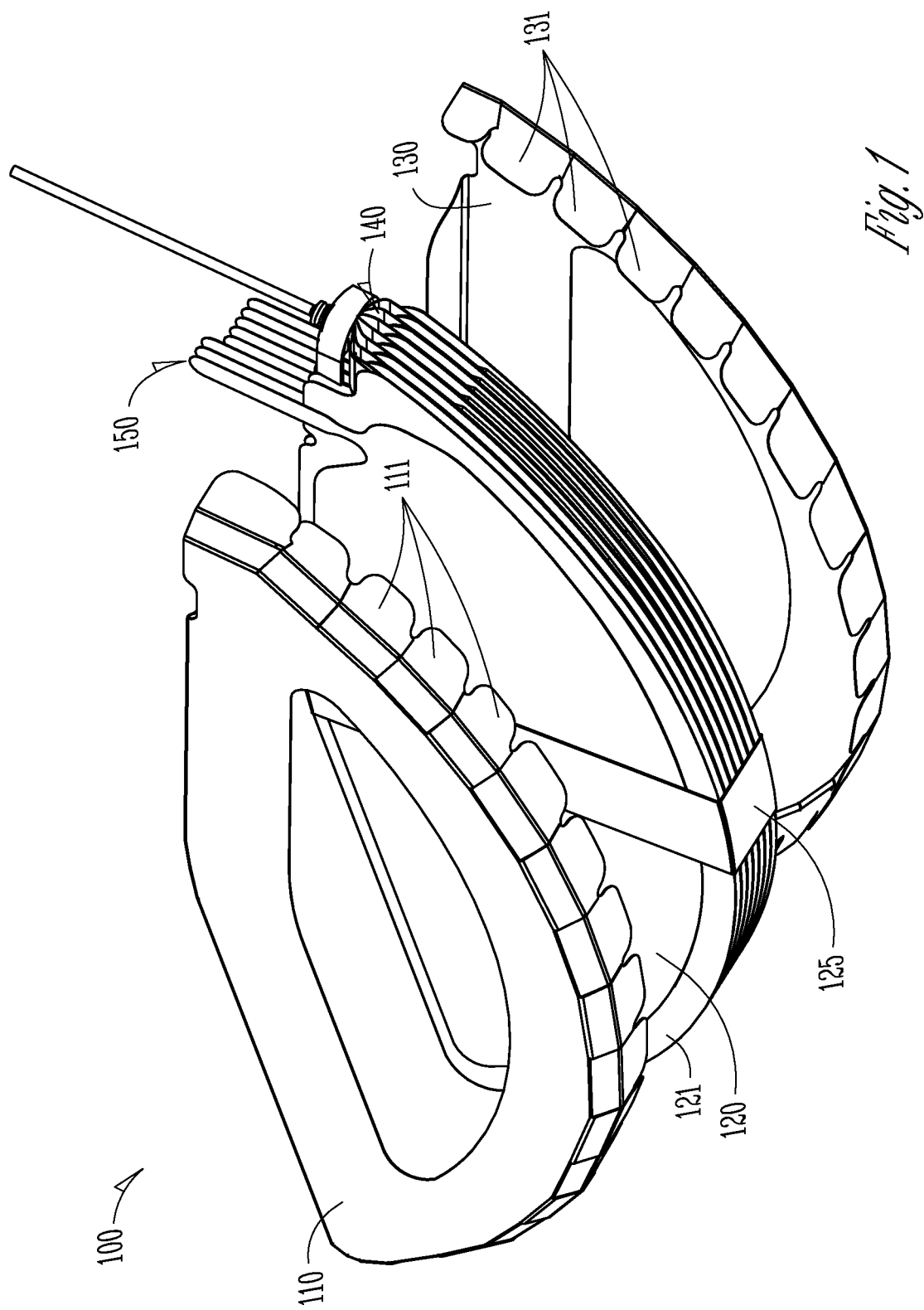
FIG. 1 illustrates a perspective view of an example apparatus including a first insulating film, a first stacked capacitor, and a second insulating film.

Clinically, a person may require a medical device (e.g., an implantable medical device) to be implanted within their body to address a medical condition. For example, a pacemaker can be implanted to provide pacing stimulation to the heart. An implantable cardiac resynchronization therapy (CRT) device can deliver pacing pulses to two or more chambers (e.g. left and right ventricle) to synchronize the chambers of the heart. An implantable defibrillator can be implanted to monitor for arrhythmia and, when certain conditions are detected, provide defibrillation therapy. In another example, a neurostimulator can provide stimulation to one or more regions of a person's nervous system (e.g. vagus nerve or spinal cord) or to the brain. Defibrillation therapy and defibrillator components can be integrated into devices that also provide stimulation therapies, such as pacemakers, CRT devices, and neurostimulators. Implantable medical devices can range in size and function, and can be utilized in numerous other portions of the body. Implantable medical devices typically include a hermetically sealed housing and component such as circuits, a battery, low and high-energy capacitors, or other electronics that reside inside the housing.

A high-energy capacitor, such as a defibrillation capacitor, can be included in an implantable medical device and insulated from other electrical components that can be damaged by high-energy electrical discharge. The capacitor can be fabricated, for example, by stacking a plurality of anodes and cathodes (among other components) on top of each other. This fabrication process can leave the edges of the anodes and cathodes exposed (e.g., not electrically insulated), such that short circuits can occur. The capacitor can be insulated such that the anode and cathodes are unable to electrically communicate with other components such as the sealed housing, unless specifically designed to do so (e.g. when the sealed housing is used as a return electrode.

A capacitor can be insulated by manually applying thin strips of tape. However, a manual, tape-based insulating process can be labor intensive and wasteful. For example, insulation strips that are applied by hand can be misapplied to the capacitor, or otherwise improperly installed such that the capacitor is not properly insulated. In addition, poorly applied insulation strips can interfere with later fabrication processes for the implantable medical device, such as the insulation interfering with hermetically sealing the housing. The aforementioned problems can result in a reapplication of the insulation, wasted components, and/or production losses.

The present inventors have recognized, among other things, that a capacitor assembly including a plurality of anodes and cathodes can be insulated with one or more shaped films that have a number of features such as tabs or flaps that are sized and shaped to cover or insulate an edge portion of the capacitor assembly. An example assembly can include a first film on a top surface of a capacitor stack, with a first set of flaps partially covering the edges, and a second film on a bottom surface of the capacitor stack. The second film can include a second set of flaps that overlap the first set of flaps and cover gaps created between tabs on the first film.

The inclusion of the two or more set of flaps can allow for the first and second insulating films to conform to a profile of the capacitor and extend around the edge of the capacitor. In some examples, the inclusion of the first and second set of flaps can allow for the first and second insulating films to respectively couple or conform to the capacitor while eliminating excess insulating and preventing bunching (e.g., errant folds or wrinkles) of the first or second insulating films. In some example, the first and second films 110 and 130 can be or include a polymer. The polymer can be electrically insulative (e.g., have a high electrical resistance). The polymer can, for example, be polyimide. The polymer can include FEP, PEEK, PTFE, PVC, or vinyl. The first and second films 110 and 130 can be pliable such that the flaps 111 and 131 can be folded or otherwise manipulated to couple with the first stacked capacitor 120.

FIG. 1 illustrates a perspective view of an example apparatus 100 including a first insulating film 110, a first stacked capacitor 120, and a second insulating film 130. The first stacked capacitor 120 can include a plurality of anodes 140 and a plurality of cathodes 150. The plurality of anodes 140 are interleaved with the plurality of cathodes 150. Stated another way, individual anodes of the plurality of anodes 140 are stacked on top of individual cathodes of the plurality of cathodes 150 such that the individual anodes and cathodes alternate in stacking order/sequence. The first stacked capacitor 120 can also include other components, such as electrodes, paper, or dielectric.

As shown in FIG. 1, the plurality of anodes 140 and the plurality of cathodes 150 can have portions that are exposed (e.g., able to allow an electrical signal to pass through to another medium or component). The first insulating film 110 and the second insulating film 130 can be used to electrically isolate the plurality of anodes 140 and the plurality of cathodes 150 of the first stacked capacitor 120 from the surrounding environment (e.g., another medium or component). Reliable insulation of the first stacked capacitor 120 can be important, for example, because if the plurality of anodes 140 were not electrically isolated, the plurality of anodes 140 could short circuit to a housing (not shown) of an implantable medical device (not shown), thereby damaging the first stacked capacitor 120 or other components within the implantable medical device. Insulation of the first stacked capacitor 120 can prevent short circuiting between the plurality of anodes 140 and the plurality of cathodes 150. The first insulating film 110 can be sized and shaped to fit against a first major face 121 (e.g. front) of the first stacked capacitor 120, and the second film 130 can be sized and shaped to fit against a second major face (e.g. back side, not shown) of the first stacked capacitor 120. The first insulating film 110 and second insulating film 120 can each include a plurality of flaps 111, 131 that are sized and shaped to extend around the edge of the first stacked capacitor 120 and overlap to insulate the first stacked capacitor 120.

The first stacked capacitor 120 can include a uniform shape (e.g., circular, square, rectangular, or the like). The first stacked capacitor 120 can include irregular shapes (e.g., comprising rounded portions of various radii, or a composite of multiple shapes, such as substantially rectangular but with rounded portions). The first stacked capacitor 120 can include a rounded portion 125. The rounded portion 125 can have a first radius of curvature. The first radius of curvature can be constant. The first radius of curvature can change along the length of the first stacked capacitor 120. The rounded portion 125 can be included in a third face of the first stacked capacitor 120. The first stacked capacitor 120 can include indentations or other features that increase the complexity of the shape of the first stacked capacitor 120 and thereby increase the complexity of insulating those indentations or other features.

Figure 2:
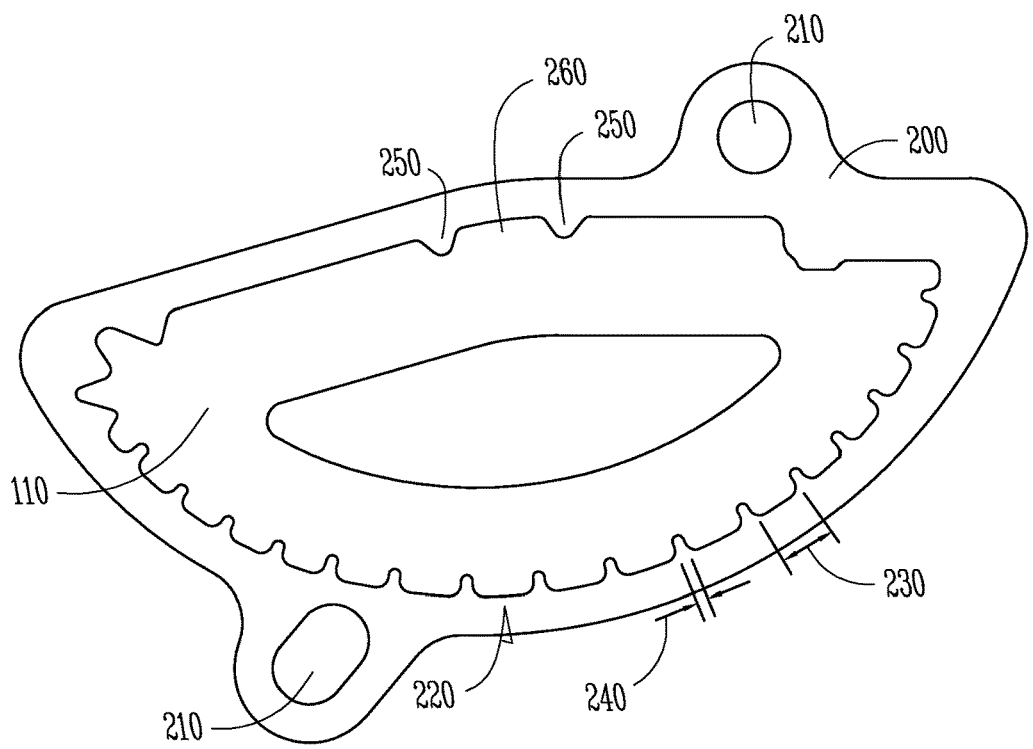
FIG. 2 illustrates a front view of an example of the first insulating film of FIG. 1 coupled with a first liner.

FIG. 2 illustrates a front view of an example of the first insulating film 110 of FIG. 1 coupled with a first liner 200. The first insulating film 110 can include an adhesive. The adhesive can be located on a first face or a second face (or both) of the first insulating film 110. The first liner 200 can be coupled to the first insulating film 110. The first liner 200 can protect the first insulating film 110 from damage (e.g., ripping, wrinkling, stretching, or the like). The first liner 200 can couple to the first insulating film 110 without the use of an adhesive, such as by van der Waals or intermolecular forces. The first liner 200 can be removably coupled to the first insulating film 110 with the use of the adhesive. The first liner 200 can be configured to easily decouple from the first insulating film 110, such as by being configured to resist bonding with the adhesive. The first liner 200 can include a removal feature, such as a tab, to ease the separation of the first liner 200 from the first insulating film 110.

The first liner 200 can include alignment indicia 210 configured to orient either the first liner 200 or the first insulating film 110 with respect to the first stacked capacitor 120. The alignment indicia 210 can be configured to mate with a die (e.g., in an automated machine) configured to apply the first insulating film 110 to the first stacked capacitor 120. The first insulating film 11 can include the alignment indicia 210.

The first insulating film 110 can include a first set of flaps 220. Each of the flaps (e.g., flap 260) can have a flap width 230. The first insulating film 110 can be sized and shaped to fit against a stacked capacitor, as shown in FIG. 1. In some examples, the flap width 230 can vary as a function of a radius of curvature (e.g., the first radius of curvature of the rounded portion 125 of FIG. 1) of an edge of the first stacked capacitor 120. Each of the flaps can have a flap length. The flap length can vary as a function of a radius of curvature of an edge of the first stacked capacitor 120. The flap length can vary as a function of the thickness of the first stacked capacitor 120. The number of flaps per unit area (e.g., flap density) can vary as a function of a radius of curvature. Each of the flaps can be spaced apart by a flap spacing 240. The flap spacing 240 can vary as a function of a radius of curvature of an edge of the first stacked capacitor 120. The first set of flaps 220 can include cutouts (e.g., cutouts 250) between each of the flaps. The cutouts can allow for the first set of flaps to couple with the first stacked capacitor 120 in a smooth and uniform manner.

For example, providing cutouts between each of the flaps allows for the flaps to cleanly couple (e.g., without folding, wrinkling, bubbling, or bunching) with the first stacked capacitor 120. The first set of flaps 220 can couple with curved portions, such as the belly portion 125, of the first stacked capacitor 120. In an example, the first insulating film 110 does not include cutouts between each of the flaps and is coupled to the first stacked capacitor. When the cutout-less first insulating film 110 is coupled to the first stacked capacitor, wrinkles, or pleats will form at the curved section because of mismatches between the geometry of the first stacked capacitor 120 and the cutout-less first insulating film 110. Providing cutouts between each of the flaps can allow for the clean coupling of the first set of flaps 220 to the first stacked capacitor 120 because excess material has been removed and space has been provided for the flaps to comply (e.g., cleanly couple) with the shape of the first stacked capacitor 120.

Figure 3:
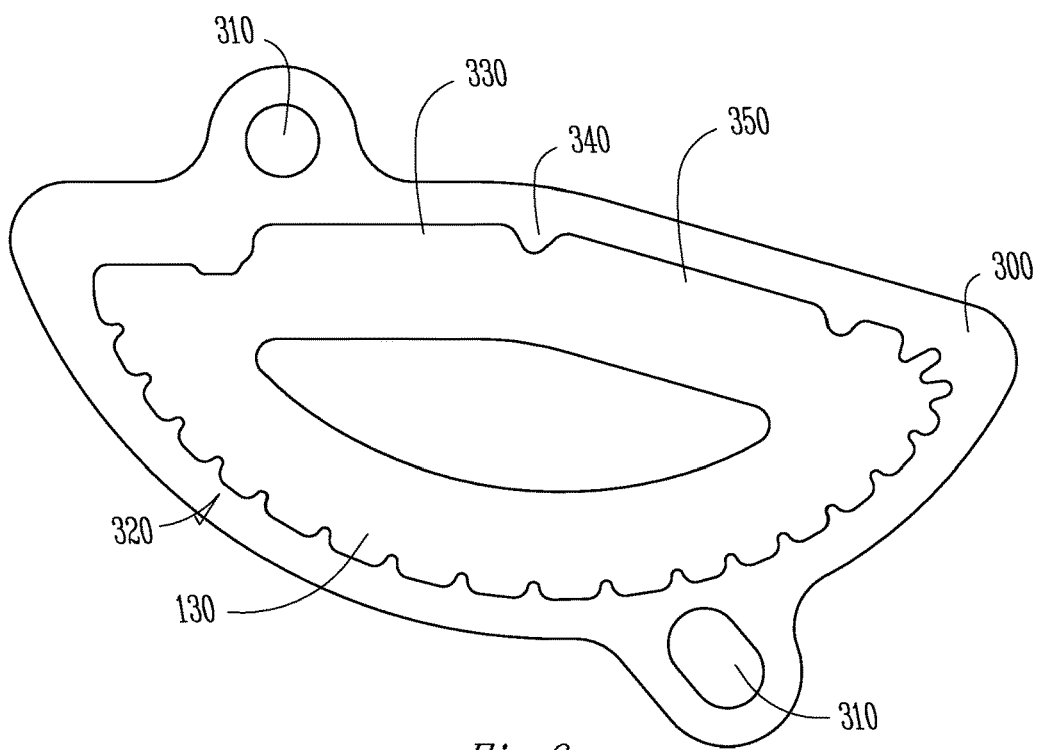
FIG. 3 illustrates a front view of an example of the second insulating film of FIG. 1 coupled with a second liner.

FIG. 3 illustrates a front view of an example of the second insulating film 130 of FIG. 1 coupled with a second liner 300. The second insulating film 130 can be configured similar to the first insulating film 110 and liner 200, with a different shape to accommodate a different placement against the capacitor. The second liner 300 can be shaped to be compatible with the shape of the second insulating film 130. The second liner 300 can be the inverse of the first liner 200. Stated another way, the second liner 300 can be the opposite side of the first liner 200 shown in FIG. 2 (and coupled to the first insulating film 110). In some examples, the second liner 300 can be the mirror image of the first liner, and the second film 130 can be the mirror image of the first film 110. In some examples, the parts can be the same shape, but with adhesive applied to a different side of the film or liner.

As shown in FIGS. 1 and 3, the second insulating film 130 can include a second set of flaps 320. The second set of flaps 320 can be configured similarly to the first set of flaps 220, such as to include varying flap widths or cutouts between flaps. However, the second set of flaps 320 can be configured to cover the spaces (e.g., the cutouts) between flaps of the first set of flaps 220. For example, as shown in FIG. 2, the first set of flaps 220 can include the cutouts 250. The second set of flaps 320 can include flaps 330 and 350. The flaps 330 and 350 can be configured to cover the cutouts 250 when the first and second sets of flaps 110 and 130 are coupled to the first stacked capacitor 120 (not shown).

Conversely, the first set of flaps 220 can be configured to cover the spaces between flaps of the second set of flaps 220. For example, the second set of flaps 320 can include a cutout 340. As shown in FIG. 2, the first set of flaps 220 can include the flap 260. The flap 260 can be configured to cover the cutout 340 when the first and second sets of flaps 110 and 130 are coupled to the first stacked capacitor 120 (not shown). Although cutouts 250 and 340 are discussed herein, other cutout and flap combinations are possible such that the first set of flaps 220 covers spaces (e.g., cutouts) between the second set of flaps 320, or vice versa.

Figure 4:
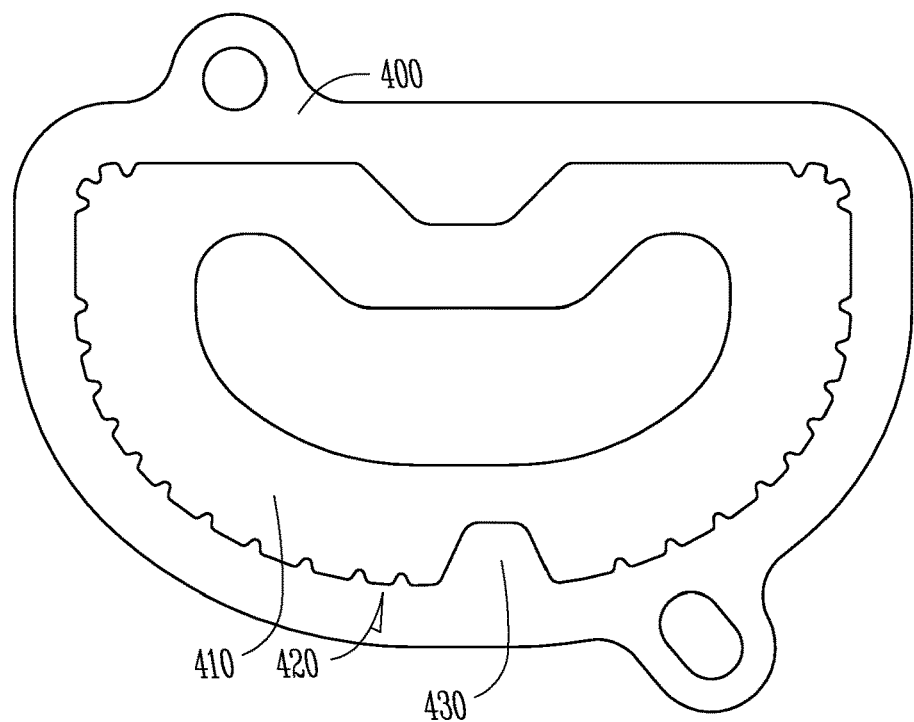
FIG. 4 illustrates a front view of an example of a third insulating film coupled with a first liner.

FIG. 4 illustrates a front view of another example of a first insulating film 410 coupled with a first liner 400. Similar to the first insulating film 110 shown in FIGS. 1 and 2, the first insulating film 410 can include a first set of flaps 420. The first set of flaps 420 can include a variable flap width, a variable flap length, or a variable flap spacing. The first set of flaps can include cutouts, such as cutout 430. The first insulating film 410 can be sized and shaped for use with capacitors, such as the second stacked capacitor 620 of FIG. 6, for example. The flap width and the flap spacing of the first insulating film 410 can differ from the flap width and spacing of the first and second insulating film 110 and 130. The location of cutouts, such as the cutout 420, in the first insulating film 410 can differ from the location of cutouts (e.g., cutouts 250 and 340 of FIGS. 2 and 3, respectively) of the first and second insulating films 110 and 130.

Figure 5:
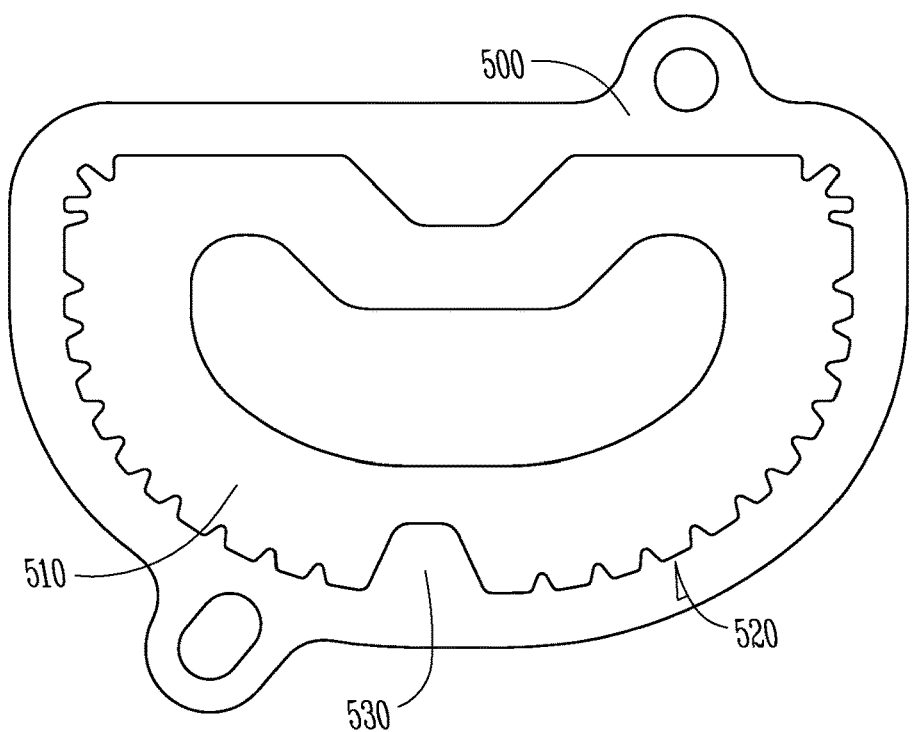
FIG. 5 illustrates a front view of an example of a fourth insulating film coupled with a second liner.

FIG. 5 illustrates a front view of an example of a second insulating film 510 coupled with a second liner 500. Similar to the first insulating film 130 shown in FIGS. 1 and 3, the second insulating film 510 can include a second set of flaps 520. The second set of flaps 520 can include a variable flap width, a variable flap length, or a variable flap spacing. The second set of flaps 520 can include cutouts, such as cutout 530. However, the second insulating film 510 can be configured to couple with other capacitors (e.g., the second stacked capacitor 620 of FIG. 6) than the first or second set of flaps 110 and 130. The flap width and the flap spacing of the fourth insulating film 410 can differ from the flap width and spacing of the first, second, and third insulating films 110, 130, and 410. The location of cutouts, such as the cutout 520, in the second insulating film 510 can differ from the location of cutouts (e.g., cutouts 250 and 340 of FIGS. 2 and 3, respectively) of the first and second insulating films 110 and 130.

Similar to the first and second sets of flaps 220 and 320, the first set of flaps 420 can be configured to cover the spaces between the second set of flaps 520, and vice versa.

Figure 6:
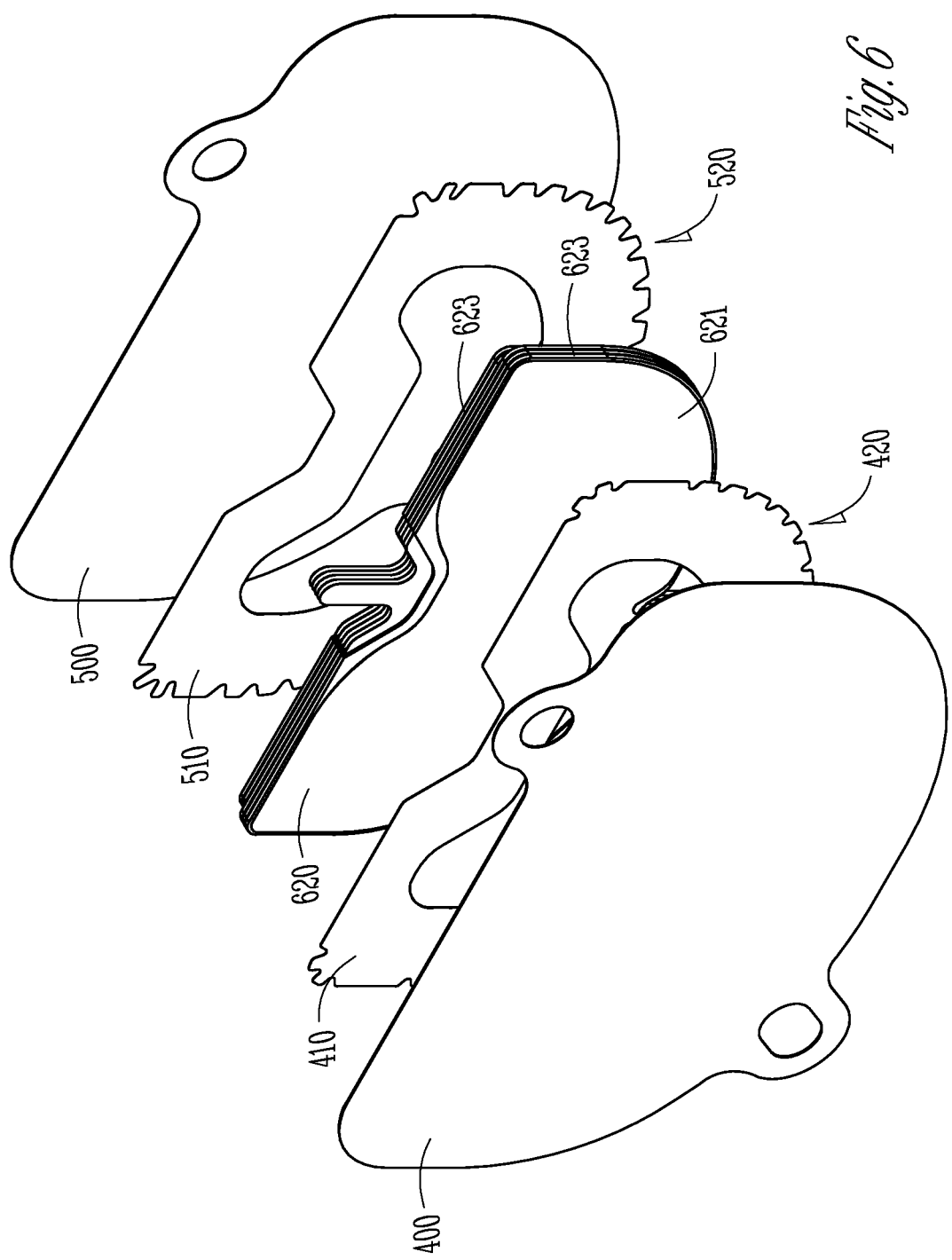
FIG. 6 illustrates a perspective view of another example apparatus including the first insulating film and the second insulating film of FIGS. 4 and 5, and a second stacked capacitor.

FIG. 6 illustrates a perspective view of another example apparatus 600 including the first insulating film 410 and the second insulating film 510 of FIGS. 4 and 5, and a second stacked capacitor 620. As shown in FIG. 6, the first and second insulating films 410 and 510 can be removably coupled to the third and fourth liners 400 and 500, respectively. The third and fourth liners 400 and 500 can be decoupled from the first and second insulating films 410 and 510, respectively, prior to coupling the first and second insulating films 410 and 510 to the second stacked capacitor 620. The third and fourth liners 400 and 500 can be decoupled from the first and second insulating films 410 and 510, respectively, once the first and second insulating films 410 and 510 are located proximate to the second stacked capacitor 620.

The first insulating film 410 can be coupled to a first major face 621 of the second stacked capacitor 620. The second insulating film 510 can be coupled to a second major face (not shown) of the second stacked capacitor 620. The first set of flaps 420 can be folded (e.g., in the same manner as the flaps 111 shown in FIG. 1) over the edges of the second stacked capacitor 620 and thereby couple the first set of flaps 420 with the second stacked capacitor 620. The first set of flaps 420 can couple with a third face 623 of the second stacked capacitor 620. Coupling the first set of flaps 420 to the second stacked capacitor 620 can insulate a portion (e.g., the third face 623) of the second stacked capacitor 620. The second set of flaps 520 can be folded over the edges of the second stacked capacitor 620 and thereby couple the second set of flaps 520 to the second stacked capacitor 620. The second set of flaps 520 can couple with the third face 623 of the second stacked capacitor 620. The second set of flaps 520 can insulate a different portion of the second stacked capacitor 620 than the first set of flaps 420. The second set of flaps 520 can cover portions of the second stacked capacitor 620 that were left exposed (e.g., the cutouts 250 of FIG. 2) when the first set of flaps 420 was coupled to the second stacked capacitor 620.

In some examples, first and second insulating films 410 and 510 can be configured such that a specified coupling sequence must be used to couple the first and second insulating films 410 and 510 to the second stacked capacitor 620. The first and second insulating films 410 and 510 can be configured such that when the first set of flaps 420 is coupled to the second stacked capacitor 620 before the second set of flaps 520, the third and fourth insulating films 410 will not interfere with additional manufacturing steps, such as hermetically sealing the capacitor assembly within an implantable medical device housing (not shown).

The coupling sequence can prevent the first and second insulating films 410 and 510 from decoupling from the second stacked capacitor 620. The coupling sequence can prevent portions of the first and second insulating films 410 and 510 from decoupling from the second stacked capacitor 620. The coupling sequence can prevent wrinkling, bunching, bubbling, dimpling, or the like from occurring during application of the first and second insulating films 410 and 510 to the second stacked capacitor 620.

For example, the second stacked capacitor 620 can be configured to mate with, or be received by, a housing of an implantable medical device (not shown). The housing can be configured as a clam-shell, such as having two housing halves that interlock, or mate, together. The housing halves can have an edge portion. The edge portion of the housing halves can interact with either the first or second insulating films 410 or 510, such as when the second capacitor 620 is placed inside a housing half.

In an example, the first major face 621 can be mated with a first housing half (e.g., the first major face 621 will be placed facing down within the first housing half and comes into contact with the first housing half). If the first set of flaps 420 were to be folded onto the third face 623 before the second set of flaps 520, edges of the second set of flaps 520 would be facing toward the first housing half (e.g., in the direction of the first major face 621). If the edges of the second set of flaps 520 faces the first housing half when the second stacked capacitor 620 is placed within the first housing half, the edge of the first housing half can interact with the edges of the second set of flaps 520, thereby peeling or otherwise acting upon the second set of flaps 520. The first housing half interacting with the second set of flaps 520 can cause the second set of flaps 520 to decouple from the third face 623. The first housing half interacting with the second set of flaps 520 can cause the second set of flaps 520 to become caught between the first housing half and a second housing half when the first and second housing halves are mated together. Alternatively, if the edges of the second set of flaps 520 faces away from the first housing half when the second stacked capacitor 620 is placed within the first housing half, the edge of the first housing half can avoid interaction with the edges of the second set of flaps 520, thereby enhancing adhesion of the second set of flaps 520 to the second capacitor 620.

Figure 7:
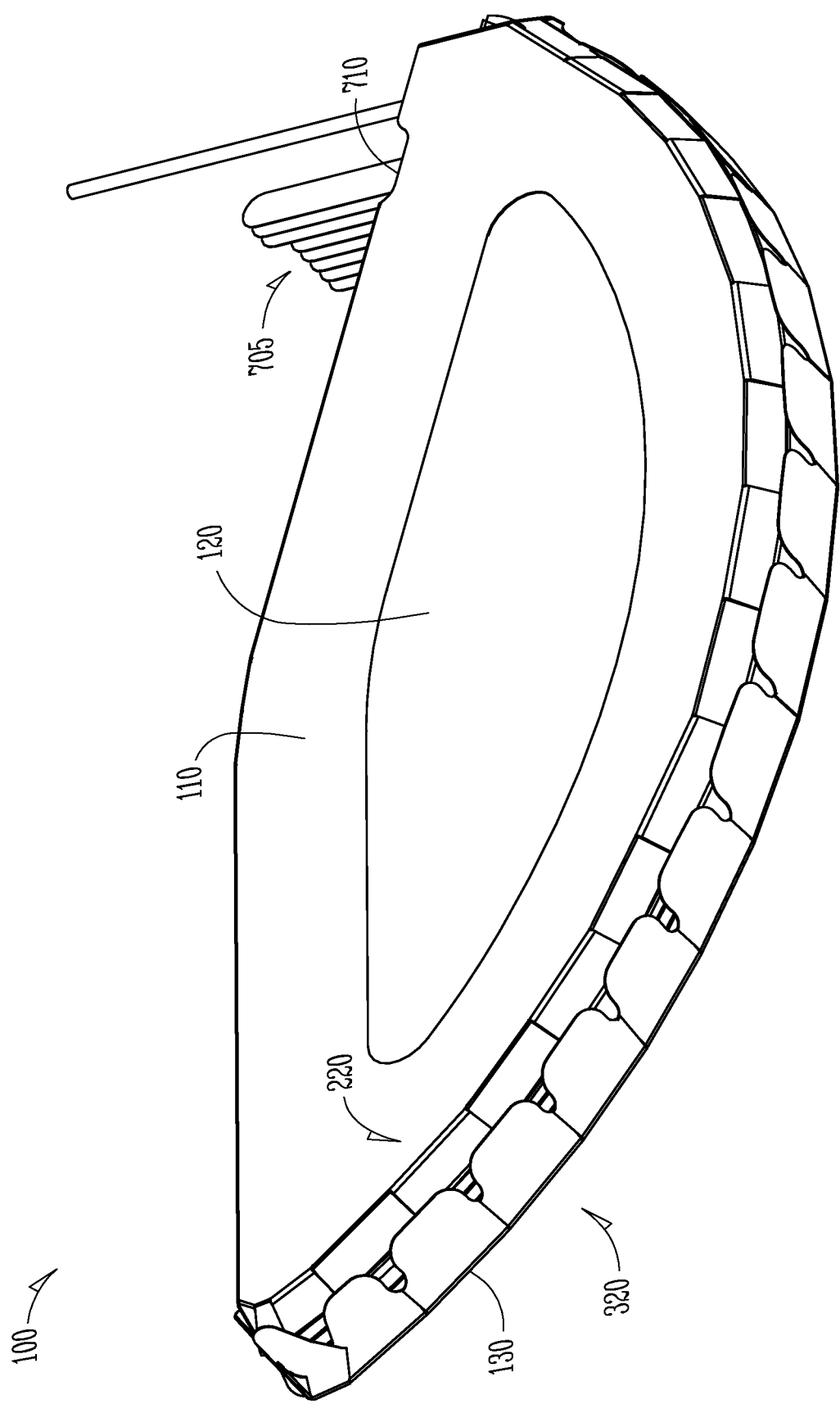
FIG. 7 illustrates a perspective view of the example apparatus of FIG. 1, wherein the first and second insulating films have been assembled with the first stacked capacitor.
Figure 8:
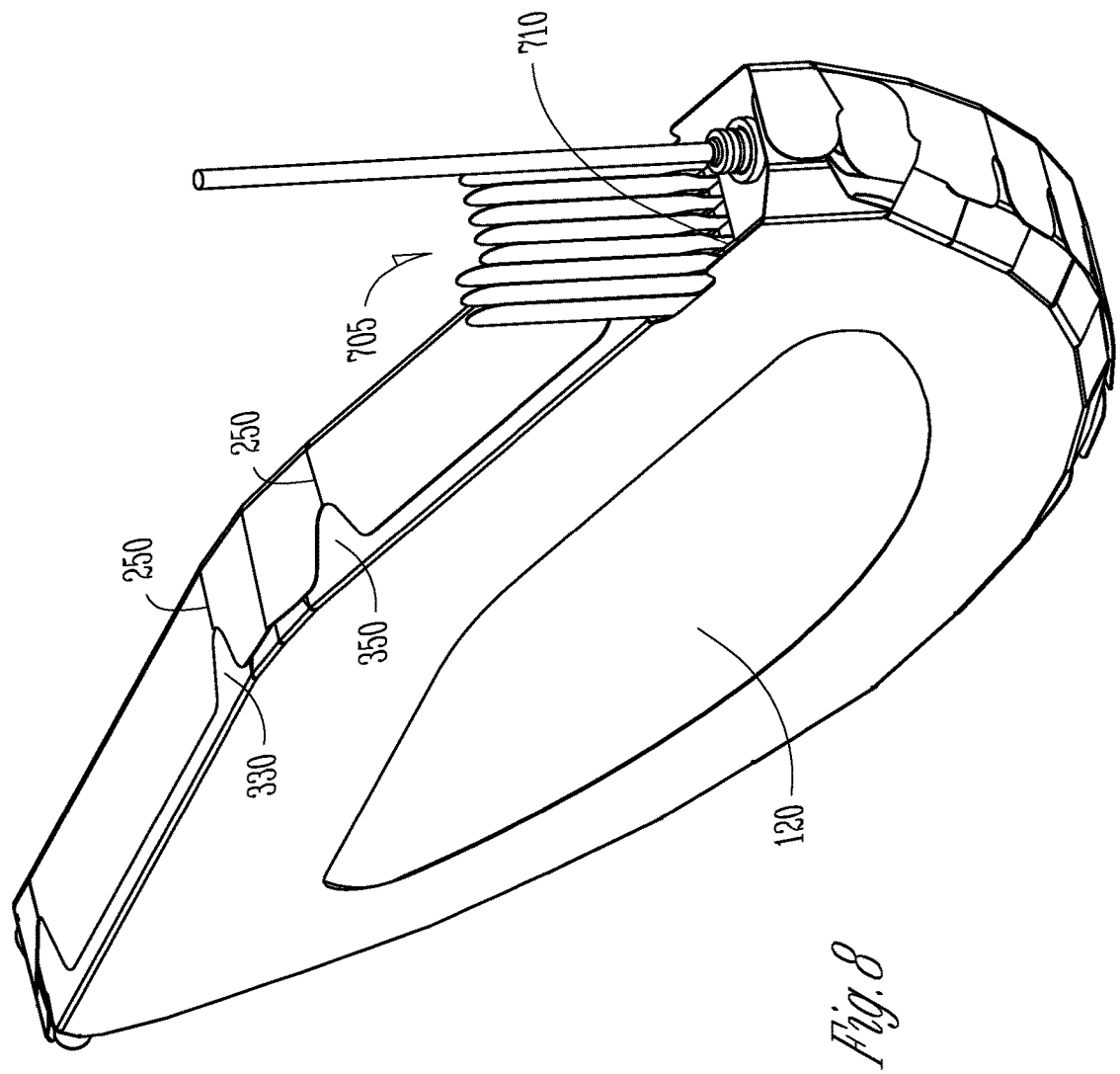
FIG. 8 illustrates another perspective view of the example apparatus of FIG. 7.

FIG. 7 and FIG. 8 illustrate perspective views of the example apparatus 100 of FIG. 1, with the first and second insulating films 110 and 130 assembled with the first stacked capacitor 120. As described herein, the first and second insulating films 110 and 130 can respectively include first and second sets of flaps 220 and 320. The first and second set of flaps 220 and 320 can be positioned against a third face (e.g., the third face 623 of FIG. 6) of the first stacked capacitor 120. In some examples, the first and second set of flaps 220 and 320 can completely cover (e.g., insulate) the third face. In some example, the first and second set of flaps 220 and 320 can also completely cover the stacked anodes and cathodes (e.g., the plurality of anodes 140 and the plurality of cathodes 150 of FIG. 1) of the first stacked capacitor 120. In some examples, the first and second insulating films 110 and 130 can cover the third face 623 (i.e. edge surface), but an outer cathode 705 can be visible through an optional cutout 710 in the insulating film. Covering the stacked anodes and cathodes can prevent electrical communication between the stacked anodes and cathodes and other components (e.g., an implantable medical device housing, not shown).

As shown in FIG. 7, the second set of flaps 320 can overlap the first set of flaps 220. The overlapping of the first set of flaps 220 by the second set of flaps 320 can cover portions of the third face of the first stacked capacitor 120 that were not covered by the first set of flaps 220 (e.g., the cutouts 250 of FIG. 2), thereby fully covering the third face. Fully covering the third face can electrically isolate portions of the first stacked capacitor 120. Additionally, and as shown in FIG. 7, the configuration of the first and second sets of flaps 220 and 320 can allow for first and second insulating films 110 and 130 to cleanly align (e.g., without folding, wrinkling, bubbling, or bunching) with the first stacked capacitor 120. In FIG. 8, the flaps 330 and 350 are visible between the cutouts 250, and the third face is completely covered by the first and second sets of flaps 220 and 330.

Figure 9:
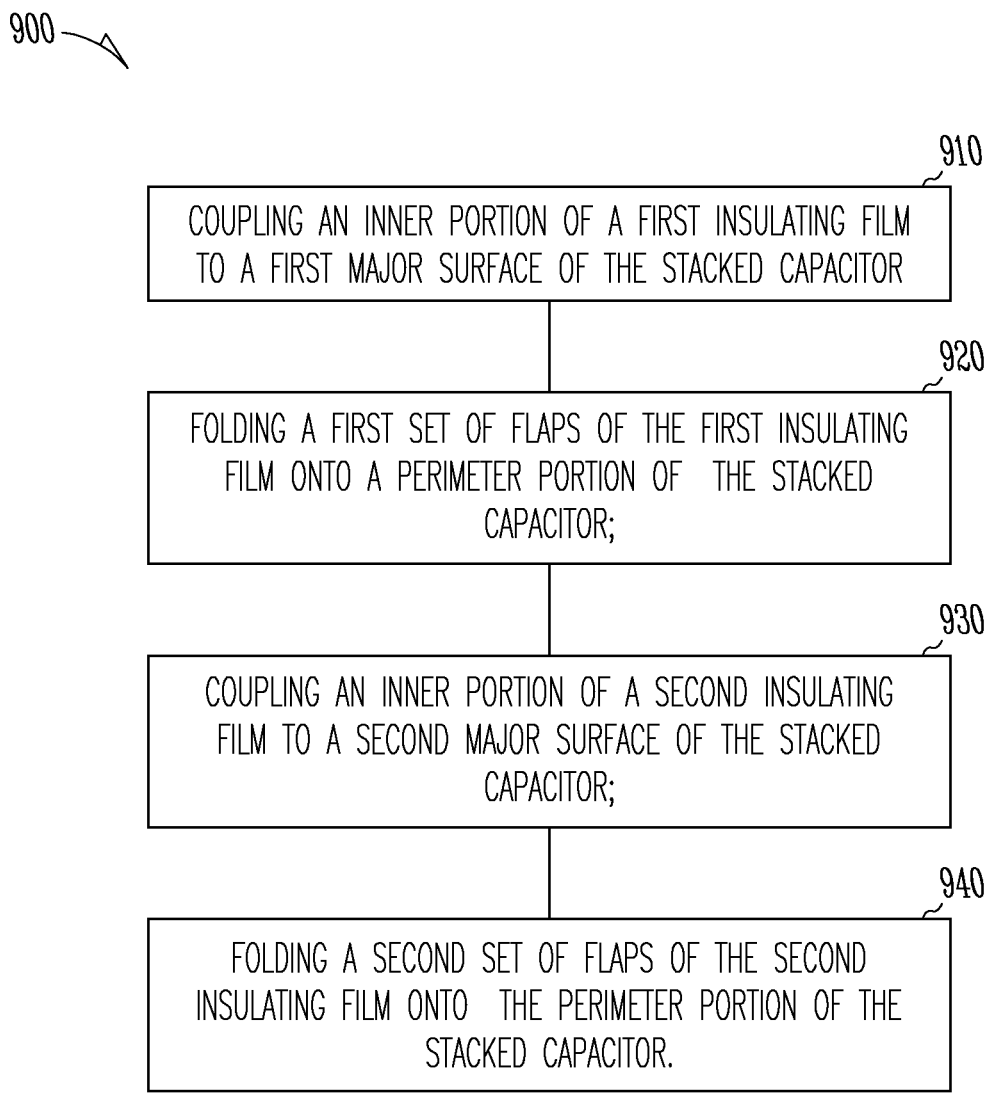
FIG. 9 illustrates an example method for insulating a stacked capacitor.

FIG. 9 illustrates an example method 900 for insulating a stacked capacitor (e.g., the first or second stacked capacitor 120 or 620 of FIGS. 1 and 6, respectively). The method 900 can include at step 910 coupling an inner portion of a first insulating film (e.g., the first insulating film 110 of FIG. 1) to a first major surface (e.g., the first major face 121) of the stacked capacitor. The method 900 can include at step 920 folding a first set of flaps (e.g., the first set of flaps 220) of the first insulating film onto a perimeter portion (e.g., the third face 623 of FIG. 6) of the stacked capacitor. The method 900 can include at step 930 coupling an inner portion of a second insulating film (e.g., the second insulating film 130) to a second major surface of the stacked capacitor. The method 900 can include at step 940 folding a second set of flaps (e.g., the second set of flaps 320 of FIG. 3) of the second insulating film onto the perimeter portion of the stacked capacitor.

The method 900 can include aligning a first insulating film with a first liner (e.g., the first liner 200 of FIG. 2). The method 900 can include aligning the first liner with the stacked capacitor. The method 900 can include folding the second set of flaps over gaps (e.g., the cutouts 250 of FIG. 2 or cutout 340 of FIG. 3) between the first set of flaps to fully cover the perimeter portion of the stacked capacitor. The method 900 can include that coupling the inner portion of the first insulating film to the first major surface of the capacitor can include bonding the inner portion of the first insulating film to the first major surface of the stacked capacitor with an adhesive.

Figure 10:
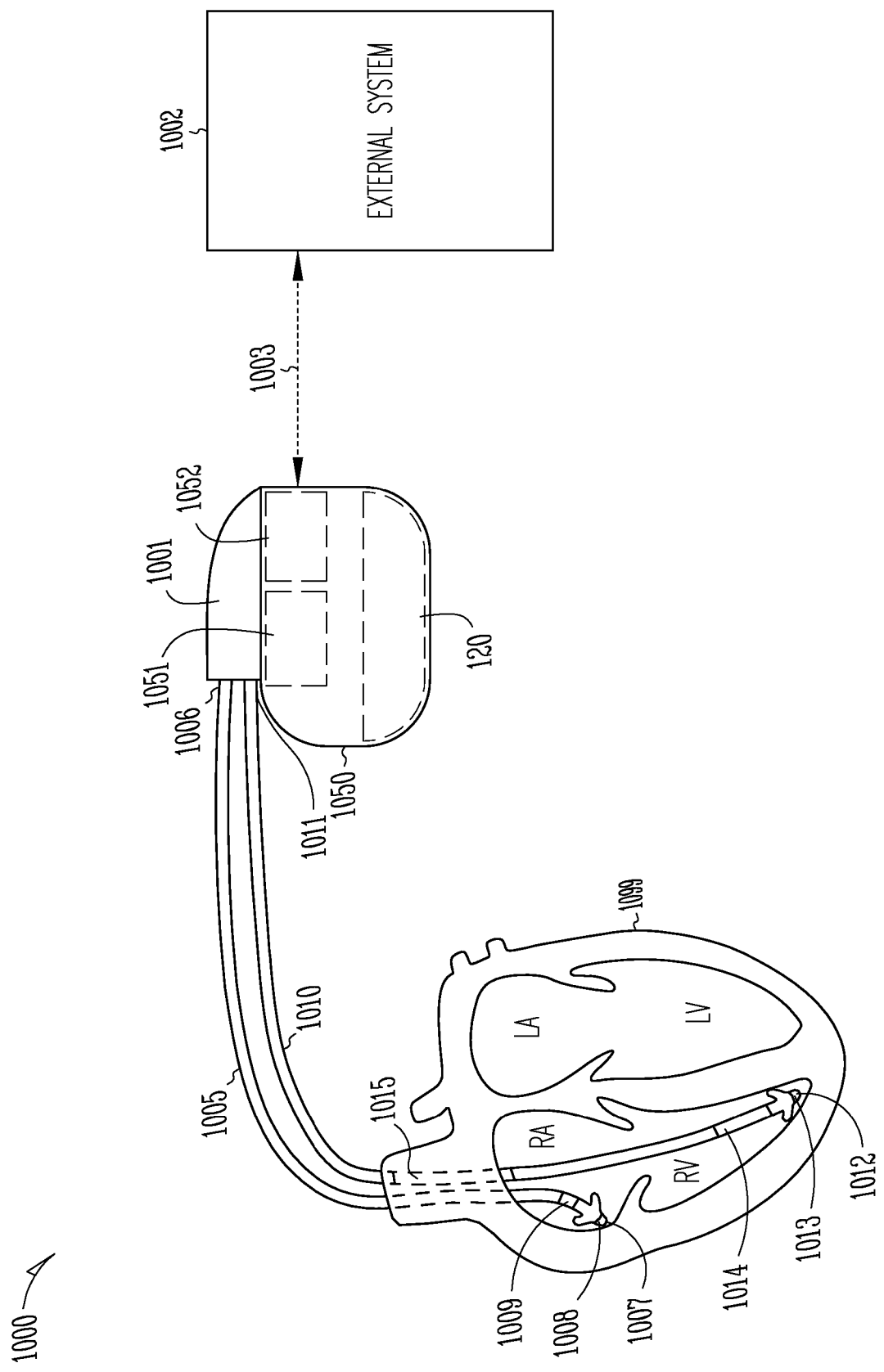
FIG. 10 illustrates a schematic view of an example system that can include an implantable medical device, an organ, and an external system.

FIG. 10 illustrates a schematic view of an example system 1000 that can include an implantable medical device 1001, an organ 1099, and an external system 1030. The organ 1099 can be a heart or a brain. The system 1000 can include an implantable medical device 1001 that is electrically coupled to the organ 1099 through leads 1005 and 1010. An external system 102 can communicate with implantable medical device 1001 via a telemetry link 103.

The implantable medical device 1001 can be an implantable medical device that performs cardiac rhythm management ("CRM") functions including delivery of cardiac pacing and cardioversion/defibrillation therapies. The implantable medical device 1001 can include a hermetically sealed housing 1050 (e.g., a hermetically sealed can), that houses an electronic circuit 1051 that can sense physiological signals and can deliver therapeutic electrical pulses. For example, the implantable medical device can deliver pacing pulses, nerve or other stimulation pulses, or a high-energy pulse such as a defibrillation shock. A high-energy shock can be delivered by discharging a first stacked capacitor 120 or a second stacked capacitor 620 that has been insulated according to the present subject matter. The hermetically sealed housing 1050 may also function as an electrode for sensing and/or pulse delivery purposes.

In one embodiment, as illustrated in FIG. 10, the electronic circuit can sense at least an atrial electrogram and a ventricular electrogram from organ 1099 and can deliver pacing and cardioversion/defibrillation pulses to organ 1099. Lead 1005 can be a pacing lead that includes a proximal end 1006 connected to implantable medical device 1001 and a distal end 1007 placed in the right atrium (RA) of organ 1099. A pacing-sensing electrode 1008 can be located at distal end 1007. Another pacing-sensing electrode 1009 can be located near distal end 1007. Electrodes 1008 and 1009 can be electronically connected to implantable medical device 1001 via separate conductors in lead 1005 to allow for sensing of the atrial electrogram and/or delivery of atrial pacing pulses. Lead 1010 can be a defibrillation lead that includes a proximal end 1011 connected to implantable medical device 1001 and a distal end 1012 that can be placed in the right ventricle (RV) of organ 1099.

A pacing-sensing electrode 1013 can be located at distal end 1012. A defibrillation electrode 1014 can be located near distal end 1012 but electrically separated from pacing-sensing electrode 1013. Another defibrillation electrode 1015 can be located at a distance from distal end 1012 for supraventricular placement. Electrodes 1013, 1014, and 1015 can be electrically connected to implantable medical device 1001 via separate conductors in lead 1010. Electrode 1013 and 1014 can allow for sensing of the ventricular electrogram and/or delivery of ventricular pacing pulses. Electrodes 1014 and 1015 can allow for delivery of ventricular cardioversion/defibrillation pulses. The functions of these electrodes are discussed above by way of example and not by way of limitation. Other ways of using these electrodes are possible as understood by those of skill in the art.

The implantable medical device 1001 can include an anti-tachyarrhythmia system 1052 that uses a unified atrial tachyarrhythmia rate threshold. Anti-tachyarrhythmia system 1052 includes a plurality of functional modules each configured to be activated and deactivated by programming implantable medical device 1001 through external system 1002. The functional modules each use an atrial tachyarrhythmia rate threshold that is set to a unified value. In one embodiment, this unified value is programmable by the user using external system 1002.

External system 1002 allows for programming of implantable medical device 1001 and receives signals acquired by implantable medical device 1001. The programming of implantable medical device 1001 includes the selection of the functional modules and the programming of the unified value for the atrial tachyarrhythmia rate threshold, as further discussed below, with references to FIGS. 5 and 6. In one embodiment, external system 1002 includes a programmer. In another embodiment, external system 1002 is a patient management system including an external device in proximity of implantable medical device 1001, a remote device in a relatively distant location, and a telecommunication network linking the external device and the remote device. The patient management system provides for access to implantable medical device 1001 from a remote location, such as for monitoring patient status and/or adjusting therapies.

In one embodiment, telemetry link 1003 is an inductive telemetry link. In an alternative embodiment, telemetry link 1003 is a far-field radio-frequency telemetry link. Telemetry link 1003 provides for data transmission from implantable medical device 1001 to external system 1002. This may include, for example, transmitting real-time physiological data acquired by implantable medical device 1001, extracting physiological data acquired by and stored in implantable medical device 1001, extracting therapy history data stored in implantable medical device 1001, and extracting data indicating an operational status of implantable medical device 1001 (e.g., battery status and lead impedance). Telemetry link 1003 also provides for data transmission from external system 1002 to implantable medical device 1001. This may include, for example, programming implantable medical device 1001 to acquire physiological data, programming implantable medical device 1001 to perform at least one self-diagnostic test (such as for a device operational status), programming implantable medical device 1001 to run a signal analysis algorithm (such as an algorithm implementing a tachyarrhythmia classification method discussed in this document), and programming implantable medical device 1001 to deliver pacing and/or cardioversion/defibrillation therapies.

The circuit of implantable medical device 1001, including its various elements discussed in this document, may be implemented using a combination of hardware and software. In various embodiments, each element of implantable medical device 1001 discussed in this document may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. For example, a "comparator" includes, among other things, an electronic circuit comparator constructed to perform the only function of a comparison between two signals or a portion of a general-purpose circuit driven by a code instructing that portion of the general-purpose circuit to perform the comparison between the two signals.

Figure 11:
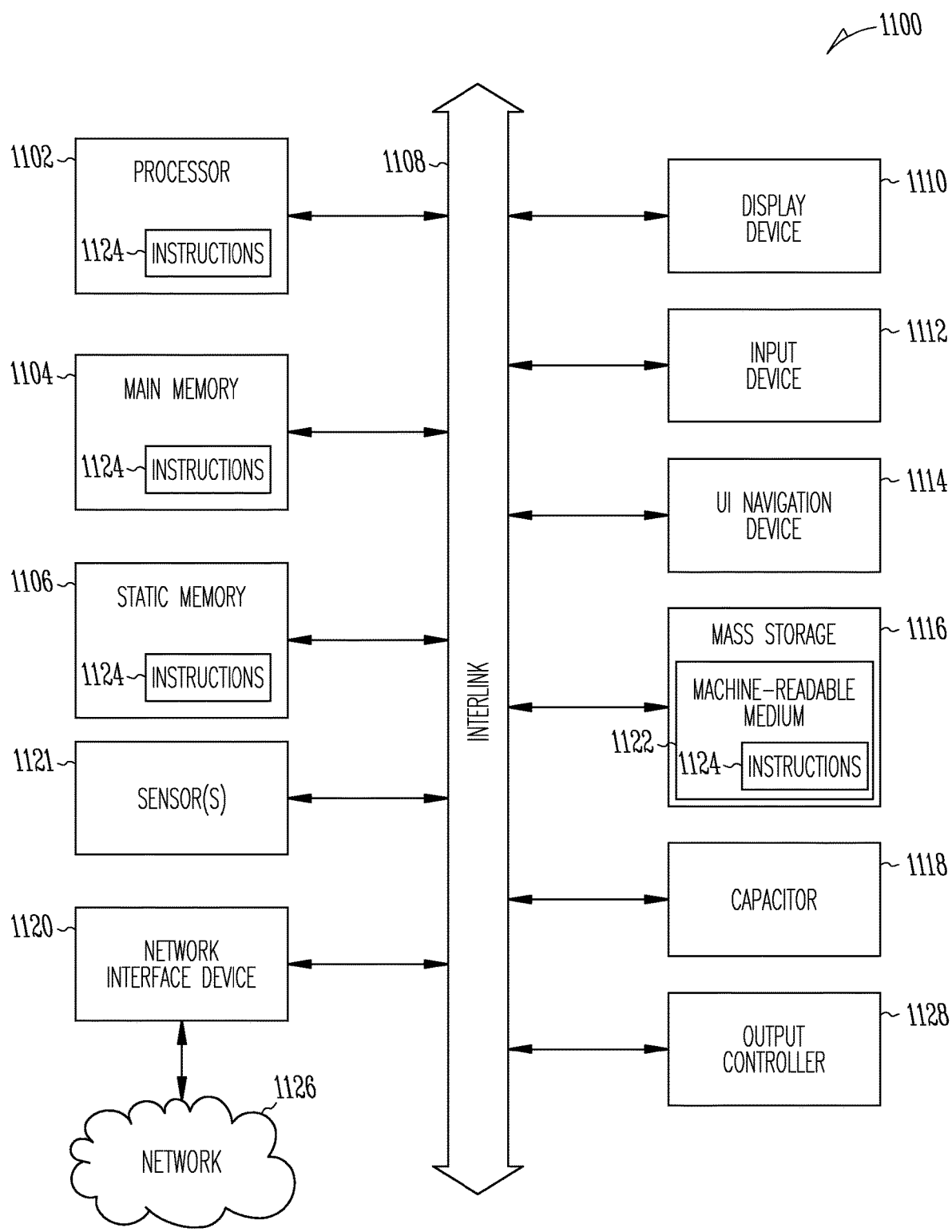
FIG. 11 illustrates a block diagram of an example machine into which an insulated stacked capacitor may be integrated upon which and any one or more of the techniques (e.g., methodologies) discussed herein may perform.

FIG. 11 illustrates a block diagram of an example machine 1100 into which an insulated stacked capacitor (e.g., the apparatus 100 of FIG. 1 or the apparatus 600 of FIG. 6) may be integrated and upon which any one or more of the techniques (e.g., methodologies) discussed herein may perform. Portions of this description may apply to the computing framework of various portions of an implantable medical device, such as implantable medical device 1001 of FIG. 10 or the external system, or an implantable device operating as part of a system. In alternative embodiments, the machine 1100 may operate as a standalone device or may be connected (e.g., networked) to other machines. For example, in a networked deployment, the machine 1100 may operate in the capacity of a server machine, a client machine, or both in server-client network environments. In some examples, portions of the machine such as stimulation therapy electrodes coupled to an output controller 1128, may be part of or coupled to an implantable device, and other portions, such as a touchscreen input device, display device, or physical ports may be part of an external (non-implanted) system.

In an example, the machine 1100 may act as a peer machine in peer-to-peer (P2P) (or other distributed) network environment. The machine 1100 may be or include a special purpose implantable or wearable device, personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation.

Accordingly, the computer readable medium is communicatively coupled to the other components of the circuit set member when the device is operating. In an example, any of the physical components may be used in more than one member of more than one circuit set. For example, under operation, execution units may be used in a first circuit (e.g., the electronic circuit 1051 of FIG. 10) of a first circuit set at one point in time and reused by a second circuit in the first circuit set, or by a third circuit in a second circuit set at a different time.

Machine (e.g., computer system) 1100 may include a hardware processor 1102 (e.g., a central processing unit (CPU), a graphics processing unit (GPU), a hardware processor core, or any combination thereof), a main memory 1104 and a static memory 1106, some or all of which may communicate with each other via an interlink (e.g., bus) 1108. The machine 1100 may further include a display unit 1110 (e.g., a raster display, vector display, holographic display, etc.), an alphanumeric input device 1112 (e.g., a keyboard), and a user interface (UI) navigation device 1114 (e.g., a mouse). In an example, the display unit 1110, input device 1112 and UI navigation device 1114 may be a touch screen display. The machine 1100 may additionally include a storage device (e.g., drive unit) 1116, a signal generation device (e.g., a piezoelectric buzzer), a network interface device 1120 such as a MICS or Bluetooth radio, and one or more sensors 1121, such as an electrode capable of detecting cardiac signals (e.g., cardiac activation or depolarization), respiration, an acoustic sensor configured to detect heart sounds, or other physiologic signals, a global positioning system (GPS) sensor, compass, accelerometer, or other sensor. The machine 1100 may include an output controller 1128, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The machine 1100 can include a capacitor 1118 (e.g., the first or second stacked capacitors 120 or 620 of FIG. 1 or 6, respectively) that has been insulated in accordance with the present subject matter. In some examples, the machine can deliver a high-energy shock (e.g., defibrillation shock) by discharging a charge in the capacitor 1118 when a specified type of arrhythmia is detected by the processor 1102 using data from one or more sensors 1121.

The storage device 1116 may include a machine readable medium 1122 on which is stored one or more sets of data structures or instructions 1124 (e.g., software) embodying or utilized by any one or more of the techniques or functions described herein. The instructions 1124 may also reside, completely or at least partially, within the main memory 1104, within static memory 1106, or within the hardware processor 1102 during execution thereof by the machine 1100. In an example, one or any combination of the hardware processor 102, the main memory 104, the static memory 1106, or the storage device 1116 may constitute machine readable media.

While the machine readable medium 1122 is illustrated as a single medium, the term "machine readable medium" may include a single medium or multiple media (e.g., a centralized or distributed database, and/or associated caches and servers) configured to store the one or more instructions 1124.

The term "machine readable medium" may include any medium that is capable of storing, encoding, or carrying instructions for execution by the machine 1100 and that cause the machine 1100 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1124 may further be transmitted or received over a communications network 1126 using a transmission medium via the network interface device 1120 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1120 may include one or more physical jacks (e.g., Ethernet, coaxial, or phone jacks) or one or more antennas to connect to the communications network 1126. In an example, the network interface device 1120 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1100, and includes digital or analog communications signals or other intangible medium to facilitate communication of such software.

Various embodiments are illustrated in the figures above. One or more features from one or more of these embodiments may be combined to form other embodiments.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical device capacitor assembly, comprising:
a capacitor including a plurality of anodes and cathodes, wherein the capacitor has a first major face, a second major face opposite the first major face, and a third face extending between the first major face and the second major face;
a first insulating film sized and shaped to cover the first major face, and including a first set of flaps sized and shaped to cover at least a portion of the third face; and
a second insulating film sized and shaped to cover the second major face, and including a second set of flaps sized and shaped to cover at least a portion of the third face,
wherein the second set of flaps overlaps at least a portion of the first set of flaps.

2. The capacitor assembly of claim 1, wherein the first insulating film is bonded to the capacitor with an adhesive.

3. The capacitor assembly of claim 2, wherein the second insulating film is bonded to the capacitor and to overlapped portions of the first insulating film with an adhesive.

4. The capacitor assembly of claim 1, wherein one or more of the second set of flaps extend over the third face and onto a portion of the third face that is covered by the first insulating film.

5. The capacitor assembly of claim 1, wherein the third face is curved.

6. The capacitor assembly of claim 5, wherein the capacitor further includes a fourth face that is not curved, and the first insulating film includes one or more flaps extending over the fourth face.

7. The capacitor assembly of claim 1, wherein each of the flaps has a flap width, and the flap width varies as a function of a radius of curvature of an edge of the capacitor.

8. The capacitor assembly of claim 1, wherein the first insulating film or the second insulating film include one or more alignment features configured to orientate the first insulating film or the second insulating film with respect to the capacitor.

9. The capacitor assembly of claim 1, wherein the capacitor has a belly portion having a first radius and a corner portion having a second radius that is less than the first radius, and further comprising belly flaps sized and shaped to cover the belly portion and corner flaps sized and shaped to cover the corner portion.

10. The capacitor assembly of claim 1, wherein the first insulating film or the second insulating film includes a polymer.

11. An implantable medical device, comprising:
an implantable medical device housing;
a pulse generator circuit in the implantable medical device housing;
a capacitor housing in the implantable medical device housing;
a capacitor in the capacitor housing, the capacitor operatively coupled to the pulse generator circuit; and
one or more insulating films extending over top and bottom portions of the capacitor, the one or more films including a first set of flaps extending down from the top portion over an edge portion of the capacitor and a second set of flaps extending up from the bottom portion over the edge portion, the first set of flaps and second set of flaps overlapping on the edge portion, and
wherein the first set of flaps define gaps between flaps of the first set of flaps, and wherein the second set of flaps extend at least partially over the gaps.

12. The implantable medical device of claim 11, wherein the one or more insulating films are configured to prevent electrical communication between the capacitor housing and the capacitor.

13. The implantable medical device of claim 11, wherein the capacitor includes a plurality of stacked cathodes and anodes, the edge portion of the capacitor defined by edges of the stacked cathodes, and wherein the first set of flaps and second set up flaps together cover the edges of the stacked cathodes to insulate the edge portion.

14. The implantable medical device of claim 11, wherein each of the flaps of the first and second set of flaps has a flap width, and the flap width varies as a function of a radius of curvature of an edge of the capacitor.

15. The implantable medical device of claim 11, wherein the capacitor has a belly portion having a first radius and a corner portion having a second radius that is less than the first radius, and further comprising belly flaps sized and shaped to cover the belly portion and corner flaps sized and shaped to cover the corner portion.

16. A method for insulating a stacked capacitor, comprising:
coupling an inner portion of a first insulating film to a first major surface of the stacked capacitor;
folding a first set of flaps of the first insulating film onto a perimeter portion of the stacked capacitor;
coupling an inner portion of a second insulating film to a second major surface of the stacked capacitor;
folding a second set of flaps of the second insulating film onto the perimeter portion of the stacked capacitor, wherein folding the second set of flaps over gaps between flaps of the first set of flaps comprises fully covering the perimeter portion of the stacked capacitor.

17. The method of claim 16, wherein coupling the inner portion of the first insulating film to the first major surface of the capacitor includes bonding the inner portion of the first insulating film to the first major surface of the stacked capacitor with an adhesive.

* * * * *